United States Patent [19]

Richman et al.

[11] 4,394,246
[45] Jul. 19, 1983

[54] ELECTROPHORESIS APPARATUS WITH FLOW CONTROL

[75] Inventors: David W. Richman, Chesterfield; Charles D. Walker, Ballwin, both of Mo.

[73] Assignee: McDonnell Douglas Corporation, Long Beach, Calif.

[21] Appl. No.: 381,049

[22] Filed: May 24, 1982

[51] Int. Cl.³ .................. G01N 27/26; G01N 27/40
[52] U.S. Cl. .............................. 204/301; 204/180 P
[58] Field of Search ............ 204/299 R, 301, 180 P, 204/180 R

[56] References Cited

U.S. PATENT DOCUMENTS 3,829,370  3/1972  Bourat .............................. 204/301
4,309,268  1/1982  Richman .......................... 204/299 R Primary Examiner—Charles F. Warren
Assistant Examiner—Gerard P. Rooney
Attorney, Agent, or Firm—Gregory A. Cone; George W. Finch; Donald L. Royer

[57] ABSTRACT

This free flow electrophoresis separation apparatus includes means for controlling the buffer flow across the separation chamber. This is useful in controlling crescent distortion of the sample streams as well as minimizing undesired pressure differentials within the apparatus. The electrophoresis separation apparatus is constructed such that two buffer flow paths are provided. The first flow path connects the outlet of the first electrode chamber with the inlet of the second inlet chamber, and the second flow path connects the outlet of the second electrode chamber with the inlet of the first electrode chamber. Each flow path is driven by separate pump means.

7 Claims, 3 Drawing Figures

ELECTROPHORESIS APPARATUS WITH FLOW CONTROL

BACKGROUND OF THE INVENTION

1. Field of the Invention

The present invention relates to an apparatus for performing a continuous free flow electrophoresis process. More particularly, the present invention relates to an apparatus for performing a continuous free flow electrophoresis procedure in which means are provided for controlling the buffer fluid flow across the separation chamber.

2. Description of the Prior Art

Electrophoresis in general is the phenomenon of the migration of charged particles or ions in a liquid carrier (buffer) medium under the influence of an electrical field. This phenomenon can be used to separate the various components of a biological sample comprised of various small particles which, by reason of different surface chemical properties, exhibit different concentrations of surface charge in the given medium. Commonly, the sample will contain protein or cell particles of very similar chemical characteristics, characteristics which would be impossible to separate one from another but for the electrophoresis separation technique. Under the influence of the electrical field within the apparatus, the electrophoretic mobilities of the various components of the sample will be different. Under the influence of the electrical field, the individual particles are rapidly accelerated in the lateral direction to approach a terminal velocity which is in equilibrium with the force of the viscous drag on the individual components. Each component will, in general, have a different lateral terminal velocity. A sample continuously introduced at some point into the sheet of liquid carrier medium (buffer) will flow in a narrow band in the absence of a potential gradient upon the apparatus. However, when a potential gradient is applied to the buffer sheet, the sample particles are separated under the influence of electrical field into the various components, depending upon the electrophoretic mobility of the respective components, the strength of the electrical field, and the length of time that the particles remain in the apparatus. Particles of similar mobility are concentrated in distinctive zones or bands which fan out from the point of sample introduction.

The present invention relates in particular to a free flow continuous electrophoresis process in which a buffer solution is made to flow freely in a uniform film or sheet through a central separation chamber defined by two parallel elongate plates. A sample is introduced into the buffer sheet at some point near the inlet to the separation chamber and an electrical potential gradient is applied across this flowing sheet perpendicular to the direction of buffer flow. The individual components within the sample then separate into narrow bands, depending upon their respective electrophoretic mobilities, and are collected from the outlet end of the separation chamber through one or more of a plurality of small tubes disposed along a collection manifold at the outlet of the separation chamber.

In present electrophoresis separation apparatus, the required electrical field is established between a pair of electrodes, one along a first lateral edge of the central separation chamber, and the other along the other lateral edge of the separation chamber. Because the buffer is usually made up of water with additional ionic species that, by their buffering action, protect the viability of the biological material being separated, the buffer fluid is electrically conductive. When the electrical field is imposed upon the conductive buffer carrier fluid, electrolysis of the water occurs, liberating hydrogen gas at the cathode electrode and oxygen gas at the anode electrode. Since the amount of gas liberated usually exceeds the amount that can be dissolved in the carrier buffer flow, undesirable byproducts are introduced into the buffer flow stream. This problem is circumvented in conventional electrophoresis separation apparatus by separating the lateral electrode chambers from the central separation chamber by ion permeable membranes and also by providing for locally increased buffer flow rates within the electrode chambers. Nevertheless, the utilization of ion permeable membranes between the electrode chambers and the central separation chamber creates several important limitations upon the separation process. Ionic species population in the buffer fluid will vary locally due to the polarization of the ion permeable membranes. The inherent electrical resistance of the membranes will create local heating of the buffer fluid. Also, pressure differentials will be created across the membranes due to electro-osmotic pumping within the separation chamber.

SUMMARY OF THE INVENTION

The apparatus of this invention provides means for controlling the fluid flow across the separation chamber in a direction parallel to the electric field. These means are applicable to conventional electrophoresis apparatus which employ ion permeable membranes to separate the electrode chambers from the central separation chamber and also to a novel electrophoresis apparatus disclosed in a companion application and assigned to the assignee of this invention which, by the nature of its construction, does not require the presence of ion permeable membranes separating the electrode chambers from the central separation chamber. Briefly, these means comprise two fluid flow paths, one connecting the outlet of the first electrode buffer chamber with the inlet of the second buffer chamber and the second connecting the outlet of the second electrode buffer chamber with the inlet to the first electrode buffer chamber. Each fluid flow path is provided with pump means which serve to circulate the buffer through the flow path and into and out of the electrophoresis separation apparatus. Since each fluid flow path has a separate pump means, the inlet and outlet flows in each flow path may be precisely controlled in relationship to each other, which in turn very closely regulates the fluid flows within the separation apparatus itself. The employment of these means in a conventional electrophoresis separation apparatus provides for the alleviation of the above-mentioned limitations to the process caused by the presence of ion permeable membranes and further improves the trans membrane pressure balance in the apparatus.

DETAILED DESCRIPTION OF THE INVENTION

As stated above, this improved electrophoresis separation apparatus is provided with means to control buffer flow across the separation chamber in a direction parallel to the electrical field. One of the main reasons for implementing and controlling cross chamber flow within the separation chamber is to compensate for and correct the crescent distortion effect. The crescent distortion effect is caused by a number of factors which are inherent in the electrophoresis process that combine to introduce distortion into the various individually deflected sample component streams. This distortion, when examined in a cross section perpendicular to the longitudinal axis of the separation chamber, assumes a crescent shape and is, therefore, most commonly referred to as crescent distortion. A more complete discussion of this distortion effect is found in U.S. Pat. No. 4,309,268 to Richman, which is incorporated herein in its entirety. Suffice it to say for this discussion, however, that the crescent distortion effect causes a marked widening of the individual component streams as they approach the outlet collection manifold and, as a result, adversely affects the efficiency of the separation process.

Therefore, by employing the improved electrophoresis separation apparatus of this invention, the crescent distortion effect may be controlled. Additionally, buffer flow within the electrode chambers may be monitored such that the inlet and outlet flows for each electrode chamber are fixed in relationship and, if so required, the total electrode buffer flow out of the apparatus can be made to equal the total electrode buffer flow into the apparatus. Further, the pressure differential across the ion permeable membrane separating the electrode buffer chambers from the central separation chamber, if such ion permeable membranes are employed, may be balanced and controlled.

Figure 1:
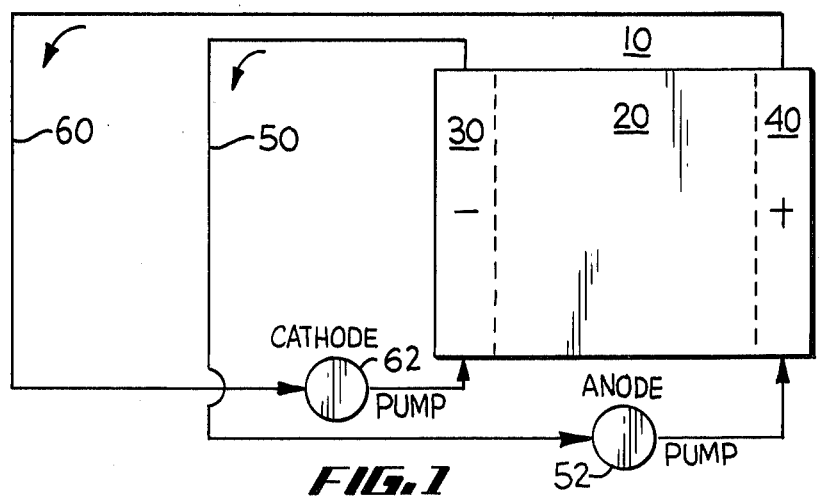
FIG. 1 is a diagrammatic view of the basic buffer fluid flow paths of the invention.

FIG. 1 illustrates in a diagrammatic view the basic layout of the improved apparatus of this invention. The electrophoresis separation chamber itself 10 is shown as separated into a central separation chamber 20, a first electrode buffer chamber 30, and a second electrode buffer chamber 40. The first electrode buffer chamber contains the cathode electrode and the second electrode buffer chamber contains the anode electrode. A first buffer fluid flow path 50 connects the outlet of the cathode chamber 30 with the inlet of the anode chamber 40. A second buffer fluid flow path 60 connects the outlet of the anode electrode chamber 40 with the inlet of the cathode electrode chamber 30. The buffer fluid is circulated through the first flow path by an anode chamber pump 52. The buffer fluid is circulated through the second buffer fluid flow path 60 by the cathode pump 62. In this basic arrangement, the buffer fluid flow paths comprise fixed volume series electrode buffer flow loops. In this case, the flow across the central separation chamber 20 from the anode chamber to the cathode chamber 30 equals the amount by which the annode buffer pump 52 flow exceeds the cathode buffer pump 62 flow. The amount of this cross chamber flow would, of course, be precisely maintained at a rate designed to correct whatever undesired distortions were present within the separation apparatus within the assistance of the cross chamber flow so introduced.

Figure 2:
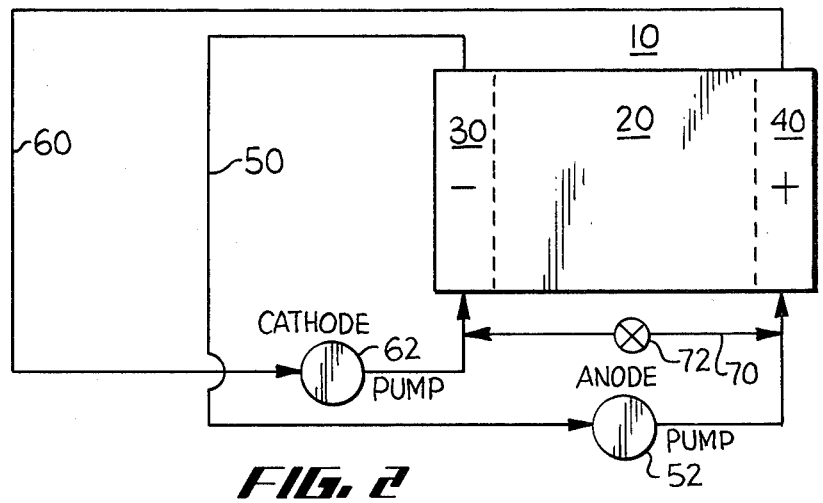
FIG. 2 is a diagrammatic of a more specific embodiment for the buffer fluid flow paths of the invention including a crossover means; and, FIG. 3 is a diagrammatic view of another specific embodiment of the buffer fluid flow paths of the invention including shunt means.

FIG. 2 is a diagrammatic view of a more specific embodiment of the buffer fluid flow path layout, specifically including a crossover means between the two buffer fluid flow loops, downstream of the two pumps. More specifically, the electrophoresis separation apparatus 10 is shown as before with a central separation chamber 20 and a first electrode buffer chamber 30 and a second electrode buffer chamber 40. The two electrode buffer fluid flow paths 50 and 60 are shown with their respective pumps 52 and 62. The crossover fluid conduit 70 is shown with an optional valve 72. The valve is optional because the valve could be omitted if the unimpeded flow path of the fluid conduit 70 was such that the fixed pressure drop inherent in the fluid flow path 70 was that required for the particular flow conditions within the apparatus. It is anticipated, however, that the valve would normally be employed, since this would lend more flexibility to the operation of the apparatus. When employed with an electrophoresis apparatus with integral ion permeable membranes separating the electrode buffer chambers from the central separation chamber, this configuration would facilitate the transmembrane pressure balance.

Figure 3:
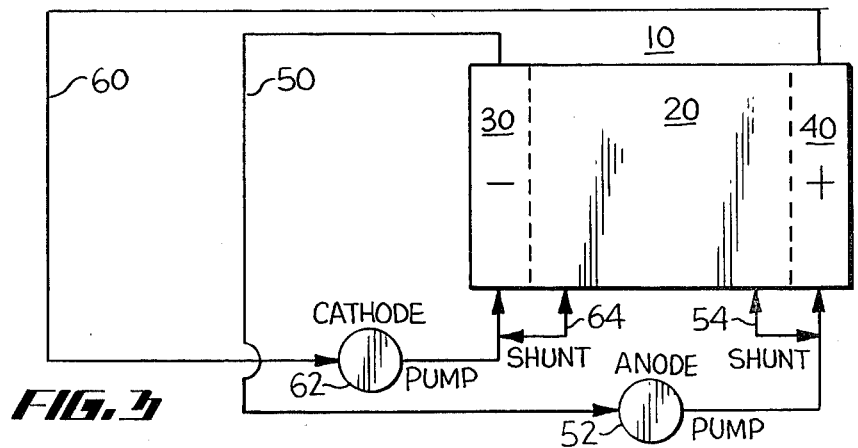

FIG. 3 shows another embodiment of the apparatus of this invention. This layout again utilizes the basic flow path configuration of FIG. 1 with the separation apparatus 10 separated into the central separation chamber 20 and the two electrode buffer chambers 30 and 40 with the electrode buffer flow paths 50 and 60 being driven by the respective pumps 52 and 62. This particular configuration also employs shunts between the central separation chamber 20 and the respective electrode buffer chambers 30 and 40. The shunts are shown in the drawing as 54 and 64. These shunts across each ion permeable membrane allow improved, independent pressure balancing. The shunts in the drawing are shown adjacent to the inlet side of the apparatus; however, they may be located anywhere along the length of the free flow apparatus 10.

What is claimed is:

1. In an apparatus for conducting a continuous free flow electrophoresis separation procedure, the apparatus comprising:

a rectilinear buffer filled separation chamber defined by two elongate spaced apart parallel plates forming a front and back to the chamber, two sides, an end comprising a collection manifold having a plurality of spaced apart collection tubes, an end comprising a buffer solution inlet manifold assembly;

two buffer filled electrode chambers, each disposed adjacent to one of the sides of the separation chamber in electrical communication therewith; and at least one sample inlet port located at or near the inlet of the chamber;

the improvement comprising means for controlling buffer flow across the separation chamber in a direction substantially parallel to an electrical field created between the electrode chambers, the means comprising first and second buffer flow paths, the first flow path connecting the outlet of the first electrode chamber with the inlet of the second electrode chamber, and the second flow path connecting the outlet of the second electrode chamber with the inlet of the first electrode chamber, the buffer solution in each flow path being driven by separate pump means.

2. The apparatus of claim 1 wherein the electrode chambers open unobstructedly into the separation chamber.

3. The apparatus of claim 1 wherein the electrode chambers are separated from the separation chamber by ion permeable membrane means.

4. The apparatus of claim 1 further comprising crossover fluid conduit means connecting the first and second flow paths.

5. The apparatus of claim 4 wherein the crossover means further comprising valve means whereby the fluid flow within the crossover means may be controlled.

6. The apparatus of claim 3 further comprising shunt means, one of which connects the first flow path with the separation chamber, and another of which connects the second flow path with the separation chamber.

7. The apparatus of claim 6 wherein the shunt means further comprise controllable valve means.

* * * * *